United States Patent [19]

Matsui et al.

[11] Patent Number: 5,298,615
[45] Date of Patent: Mar. 29, 1994

[54] ULTRA-LIGHTWEIGHT, OPEN-PORE FOAMED CELLULOSE MATERIALS WITH LARGE SURFACE AREAS, HAVING ION-EXCHANGEABLE FUNCTIONAL GROUPS INTRODUCED THEREIN

[75] Inventors: Tomomi Matsui; Kimiaki Yasuda; Michiyo Nojiri; Masanao Ohno, all of Fukui, Japan

[73] Assignees: Sakai Engineering Co., Ltd.; Agro-Systems Corporation Limited, both of Fukui, Japan

[21] Appl. No.: 680,829

[22] Filed: Apr. 5, 1991

[30] Foreign Application Priority Data

Apr. 6, 1990 [JP] Japan .................. 2-90258

[51] Int. Cl.$^5$ .................. C08B 1/00; C08L 11/00
[52] U.S. Cl. .................. 536/56; 536/57; 106/122; 422/56; 521/25; 521/61
[58] Field of Search .................. 536/56, 57; 422/56; 521/25, 61; 106/122

[56] References Cited

U.S. PATENT DOCUMENTS

| | | | |
|---|---|---|---|
| 3,912,457 | 10/1975 | Ogawa et al. | 422/56 |
| 3,914,174 | 10/1975 | Fuchs | 422/56 |
| 3,954,412 | 5/1976 | Ogawa et al. | 422/56 |
| 4,109,080 | 8/1978 | Lieser et al. | 521/25 |
| 4,144,306 | 3/1979 | Figueras | 422/56 |
| 4,189,539 | 2/1980 | Ward | 521/25 |
| 4,568,545 | 2/1986 | Mihara et al. | 514/822 |
| 4,798,847 | 1/1989 | Roesink et al. | 521/61 |
| 4,818,598 | 4/1989 | Wong | 521/25 |
| 5,002,984 | 3/1991 | Rainer | 521/25 |
| 5,169,883 | 12/1992 | Rainer | 521/25 |

*Primary Examiner*—Ronald W. Griffin
*Attorney, Agent, or Firm*—Oblon, Spivak, McCleland, Maier & Neustadt

[57] ABSTRACT

An ultra-lightweight, open-pore foamed cellulose material with an increased surface area, having ion exchangeable functional groups introduced in it. The cellulose material presents a three-dimensional network structure which, upon swollen, has a particle diameter of 0.8 to 12.0 mm, a mean pore diameter of 0.1 to 1.7 mm, a specific surface area of 1.0 to 10.0 m$^2$/g, a true density of 1.4 to 1.6 g/cm$^3$ and a porosity of 90% or greater. The ion exchangeable functional groups, for instance, may be cationic polyethyleneimine.

2 Claims, No Drawings

ULTRA-LIGHTWEIGHT, OPEN-PORE FOAMED CELLULOSE MATERIALS WITH LARGE SURFACE AREAS, HAVING ION-EXCHANGEABLE FUNCTIONAL GROUPS INTRODUCED THEREIN

BACKGROUND OF THE INVENTION

1. Field of the Invention

The present invention relates to a open-pore foamed cellulose material used as carriers for ion exchangers and culturing animal cells, which is easy to handle and has a large surface area per unit weight.

More particularly, this invention concerns a cellulose ion exchanger obtained by the introduction of an ion-exchangeable functional group in an open-pore foamed cellulose material, which is easier to handle and larger in terms of the surface area per unit weight than conventional gel-like ion exchangers. This invention is also directed to an animal cell culture carrier which is easier to handle than conventional animal cell culture microcarriers and can culture animal cells while the cells are immobilized thereon at high densities, without detriment to an environment well suited for cell growth.

2. Statement of the Prior Art

Industrial ion exchangers so far used in the art has their origin in a discovery by Adam et al in England in 1935 that condensates of phenolic compounds with formalin absorb alkalis while condensates of aniline-based compounds with formalin do acids. The commercialization began with success for the first time in Germany in 1938. Since then, they have enjoyed steadily increases indispensable to industrial purposes, inter alia, water disposal.

Most of these ion exchangers, based on resins, are of a hydrophobic nature on their surfaces. Depending upon what is ion-exchanged or, in more illustrative terms, when polymeric materials, e.g. hydrophilic biopolymers such as proteins, are ion-exchanged, they may often produce unfavourable effects due to their hydrophobic interaction with such polymers. This is for one thing, attributable to difficulty involved in elution operation, partly because ion bonds take no part in adsorption; for another, repellency takes place through electrostatic or van der Waals' force, resulting in a serious drop in adsorptivity.

Cellulose-based ion exchangers developed by Sober et al in 1954, on the other hand, are of so strong a hydrophilic nature on their surfaces, that if they are used in aqueous media, the surfaces of their supports can be taken as behaving just like an aqueous solution. To put it another way, neither adsorption nor repellency takes place through electrostatic force other than their ionic interaction with what is ion-exchanged. Therefore, such ion-exchangers have a great advantage of being able to control in an easy operation the adsorption and elution of matter, even though it is a sterically sophisticated biopolymer such as protein or lipid, in which one molecule includes hydrophilic and hydrophobic moieties with the electrostatic force therebetween being well balanced in an aqueous system. This is because no interaction but three types of electrostatic force takes place between three sets of polymer and water; polymer and functional groups the ion exchangers have; and functional groups the ion exchangers have and water.

Such ion exchangers based on cellulose supports are now commercialized in sheet (planar and filter sheets), powdery, granular and gel-like forms.

When carrying out cell culture, most of animal cells cannot proliferate without deposition onto the surface of solid matter. For that reason, some solid surface should be in store, whatever the culture scale is. In an effort to achieve the mass culture of cells in particular, every possible means is now used to increase the surface area per culture volume, thereby increasing productivity. Of these means, the most standard of all is a microcarrier culture technique, according to which microcarriers, each having a relatively large surface area, are suspended in a culture medium to increase the culture area available per culture volume to a maximum. The microcarriers, designed to culture animal cells, are obtained by forming polymers such as polysaccharides or polystyrene into beads having a particle size of 100 to 300 $\mu$m, on which the cells are to be immobilized. For promoting deposition of cells onto the microcarriers, they may be either coated thereon with collagen or positively charged by chemical synthesis. The former collagen type of carrier has an advantage of showing higher bioaffinity than does naturally occurring collagen, whereas the latter charge type of carrier has several advantages of being able to immobilize floating cells which cannot otherwise be fixed in place and capable of being repeatedly used after the removal of cells using such enzymes as a protease etc. Thus, both types of carriers may be selectively used depending upon what they are used for. The charge type of carrier is prepared by the introduction of ternary amino groups represented by a diethylaminoethyl group or quaternary amino groups as cations, typically available in the trade names of Cytodex 1 and Cytodex 2 made by Pharmacia Co., Ltd.

Having one limited use in view of morphology, currently available cellulose ion exchangers may be used on laboratorial scales but have a disadvantage of being often unsuited for use at an industrially extensive scale.

In brief, sheet-form ion exchangers are used in such a way that paper filters are used. For instance, they have been primarily employed as the immobilizing layers for paper chromatography. They may also be used possibly in another way; they may be packed in columns through fluids flow for ion exchange, wherein an ultrafiltration membrane would be spirally found as the immobilzing film for the so-called column chromatography. However, experience teaches that they cannot be used for that purpose, since there is possibility that the film may break for lack of strength and by the force generated by the flowing of fluids.

Even when they are applied to filtration according to the average procedure of using paper filters, it is impossible to make the filtration area larger than the required space, if they are used in a planar form, thus failing to increase the ion exchange capacity. For this reason, they cannot be used without subjecting them to special morphological treatments.

Powdery ion exchangers may possibly be used as the fixed layer for thin-layer chromatography. However, such use has been rarely made for the fixed layer for column chromatography, in which they are packed for the ion exchange of a sample fluid, because the size of the particles renders it impossible to increase the flow rate of the sample fluid and to enhance the ion exchange efficiency.

The powdery ion exchangers are also ill suited for use with the so-called batchwise systems wherein they are put directly into a sample fluid to be ion exchanged, thereby selectively adsorbing the required substances from the sample fluid. This is because not only is the recovery of the necessary substances timeconsuming but their washing takes too much time as well.

Thus, these two types of ion exchangers may have found their use for analytical purposes alone, as there is clear-cut evidence that they are not well fit for use at an extensive scales.

On the other hand, granular or gel-form ion exchangers have been primarily used as chromatographic fixed layers in which they are packed, or for selectively adsorbing the required substances from a sample fluid in which they are put. However, their use is limited to narrow conditions (to such low flow rates so as not to produce pressure in a state of low ionic strength) because of the following demerits. For one thing, they are crushed flat due to their low physical strength when they receive the pressure or shear force generated by increased flow rates or stirring; for another, they are likely to contract or change in diameter when sample fluids of high ionic strength are used with them, giving rise to changes in their packing in columns and to channeling.

From the practical standpoint, limited use is not desirable, since it makes little contribution to the advancement of technology. Especially when a certain type of technology has limitations to scaling up, there is only limited use, e.g. analytical use, making poor its future industrial prospects.

Turning now to animal cell culture carriers, the most popular standard ones are a microcarrier having such a large surface area as to mass culture cells. However, that microcarrier is still less satisfactory in terms of the surface area. Thus, there is a strong demand among various animal cell-related industries for the development of a carrier enabling cell culture to be carried out at much higher densities. Moreover, when microcarriers are used with turbulently flowing culture solutions or excessively packed in culture solutions, there is an increased chance of their colliding with one another with large impact, so that the immobilized cells suffer damage to such an extent that they cannot survive. In the case of microcarriers, these problems are attributable to the fact that it is only their surfaces, not at some place in them, where cell immobilization takes place.

Taken altogether, we have reached the conclusion that the basic defects of cellulose ion exchangers and animal cell culture carriers can all stem from their morphological construction.

SUMMARY OF THE INVENTION

A main object of this invention is to overcome the problems with the prior art cellulose ion exchangers and animal cell culture carriers so far put to practical use and commercialized, that they are clumsy and used on only limited scales, by providing a new version of material which can be applied to industrial purposes at an extensive scale.

In order to achieve this object, we have studied a cellulose support having the following features:
(1) Easy to handle,
(2) Excelling in water permeability,
(3) Having a larger surface area per unit weight, and
(4) Having an increased physical strength.

As a result of researches and investigation, we have now found that an open-pore foamed cellulose material is effective for such a cellulose support.

The material according to this invention may be prepared by mixing small amounts of reinforcements and cell-forming crystalline substances with viscose obtained by chemical treatments of high-purity pulp made from wood and putting the mixture in a mold wherein it is heated and then cooled down for solidification, alternatively adding the mixture dropwise into a solidifying liquid, thereby obtaining beads.

With the thus obtained open-pore foamed cellulose material, the following features can be abtained.

By using this material as an ion exchanger support, it is possible to facilitate separation of liquid from the ion exchanger. Moreover, it is possible to use the ion exchanger in a batchwise manner because of standing up to pressure increases with an increase in flow rates and shear force generated by stirring and to realize a more increased ion exchange capacity through its increased surface area.

By using this material as an animal cell culture carrier support, it is possible to provide a rapid feeding of nutrients and oxygen from a culture solution to cells. This is because the culture solution penetrate easily through the carrier by way of a number of continuously crisscrossed fine pores. In this case, however, the pore diameter should be regulated to 0.1 to 1.7 mm. On the other hand, spodogenous matters produced by cells can be so rapidly removed that the cells can grow not only on the carrier but also all through the carrier. Such a particular constructional feature enables the specific surface area to be about 10 times greater than that of the conventional microcarrier, only the surface of which is available for cell deposition, thus making it possible to immobilize cells at much higher densities. This spongy open-pore foamed construction also protects cells within it, absorbing impacts produced by collisions among the bead carriers. Thus, it is very unlikely that cells may suffer damages by collisions among the bead carriers caused by the flowing of a culture solution. Likewise, that construction protects cells against a large shear force occurring in an incubator such as a spinner flask, so that its revolutions per minute can be increased until sufficient flow rates are achieved. Such effects make it possible to pack the present carriers at a density higher than has been possible with conventional carriers.

The cellulose forming part of the open-pore foamed cellulose material is of a surface hydrophilic nature so strong that its surface can behave just like an aqueous solution, if it is used in an aqueous system, and shows a favorable affinity to biopolymers such as proteins and cells. In addition, since the cellulose contains a variety of hydroxyl groups in its molecules and presents a structure well-suited for introducing various functional groups therein, cellulose ion exchangers and animal cell culture carriers can be easily obtained from cellulose by introducing ion-exchangeable functional groups therein. The ion-exchangeable functional groups, for instance, include groups containing one nitrogen atom such as primary, secondary, tertiary amine groups and quaternary ammonium groups represented by aminoethyl, diethylamino and triethylamino groups as well as cyano, thiocyanato and hydroxyamino groups; groups containing two or more nitrogen atoms such as those represented by ureido, amidino, guanidino and polyethyleneimine groups, heterocyclic groups represented by pyrrolyl, pyridyl, piperidyl, quinolyl and morpholinyl groups, and nitrogen atom-containing crown compounds represented by azacrown and cryptand; oxygen atom-containing groups such as carboxyl groups represented by carboxymethyl and iminodiacetic acid groups, heterocyclic groups represented by a furyl group, cyclic ether represented by 18-crown-6 and carbonyl groups represented by a hydroxamic acid group; phosphorus atom-containing groups such as those represented by a phospho group; groups containing one sulfur atom such as those represented by mercapto and sulfo groups: and groups containing two sulfur atoms such as those represented by a dithiocarboxy group and hetercyclic groups such as those represented by a thienyl group.

Of these ion exchangeable functional groups, it is a polyethyleneimine group—formulated below—that is best-suited for the animal cell culture carrier of this invention.

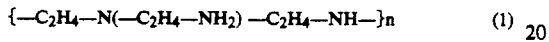
{—C$_2$H$_4$—N(—C$_2$H$_4$—NH$_2$) —C$_2$H$_4$—NH—}n   (1)

Polyethyleneimine is a transparent, viscous, water-soluble polymer obtained by polymerization in the presence of an acid catalyst and having a highly branched tree structure. Reference is here made to the reasons why the polyethyleneimine group is the best-suited functional group to be introduced in the animal cell culture carrier of this invention. For one thing, it can improve cell deposition by the feature to be described later; for another, it can minimize an adverse influence that synthetic ion exchangeable functional groups have on cells. In other words, it is desired that the amount of non-natural or synthetic functional groups to be introduced be reduced as much as possible. Polyethyleneimine, which has the highest ionization density among existing polymer materials, is capable of receiving cells in the least amount, and is said to be a more cell-receptive but less cytotoxic carrier for carrying animal cells. Straight-chain functional groups are likely to dissolve in a culture solution when their molecular chains are damaged and cut off, because they are eluted at one end not bonded to carriers. Due to its branched structure in which its terminals are all bonded to carriers, however, the polyethyleneimine group is hardly set free. Referring on the one hand to functional groups introduced in ordinary microcarriers, monomers or dimers of ternary or quaternary amino groups are so bonded together that low-molecular weight straight-chains can extend from the carriers. Once the bonded regions have been damaged and broken for some unknown reasons, the functional groups may be liberated, producing an adverse influence upon the growth of cells. Referring on the other hand to low-molecular weight functional groups introduced in usual microcarriers, their molecular chains extending from the carriers are so short that charges are distributed on the carriers' surfaces alone. Thus, the adsorption space required for immobilizing cells onto the carriers is limited to the carriers' surfaces alone. By contrast, polyethyleneimine is allowed to be present not only on the surface of the carrier material but also in a space more or less separate from the carriers, leading to an improvement in adsorption efficiency and so resulting in an increase in capability of receiving cells.

Making use of their adsorptivity, ion exchangers are used for recovering valuable matter, removing impurities, discoloration and other purposes. The open-pore foamed cellulose ion exchanger of this invention is characterized by standing up to industrial use. In addition, it may possibly find use not only in general chemical industries but in food industries as well, since naturally occurring materials used as the starting materials are excellent in terms of bioaffinity and toxically harmless. One example of the open-pore foamed cellulose ion exchanger of this invention is ECTEOLA cellulose having triethanolamino groups introduced in it. Generally available ECTEOLA cellulose has a total exchange capacity of 0.2 to 0.4 meq/g, but the BCTEOLA cellulose of this invention shows a total exchange capacity as high as 1.0 meq/g.

EXAMPLES

The present invention will now be explained specifically but not exclusively with reference to some examples in which the ECTEOLA/open-pore foamed cellulose combination is used.

EXAMPLE 1 Protein Adsorption Test

Prior to experimentation, an OH type of ECTEOLA/cellulose ion exchanger sample is provided.

A precisely weighed 1 g of the undried ECTEOLA/cellulose open-pore foamed sample is placed in an open column, which is then treated with a total amount of 1 liter of 2N-NaOH for 2 hours. After the completion of that treatment, NaOH residues in the column are flushed away, and deionized water washing is repeated until the washings show no alkaline sign. The thus treated sample is used for subsequent testing, while remaining undried.

Apart from this, a precisely measured constant amount of the sample is dried at 105° C. for 6 hours to find the weight of the dried matter. The water content is then found by the following equation:

Water Content=(Weight Before Drying−Weight After Drying)/(Weight Before Drying)

Human serum albumin (made by Wako Junyaku K.K.) is dissolved in deionized water and regulated to a concentration of 0.1% (w/v) at about pH 6.0.

Forty (40) ml of the 0.1% albumin solution are poured in each of two 100-ml volume flasks, one of which is used as a blank. Put in another flask is the OH type of the sample.

After gentle stirring, the flasks are allowed to stand overnight. The carriers are treated through a glass filter and washed with several portions of deionized water. After that, the filtrate combined with the washings is regulated with 0.1 N HCl to pH 6.0 to measure their total liquid weight.

The absorbances of the blank and test solution are measured by colorimetry at 280 nm. The adsorptivity is then found by the following equations.

Amount of Protein Not Adsorbed (mg)=(Absorbance Of Testing Liquid/Absorbance of Blank)×Total Liquid Weight (ml)×1 mg/ml.

Adsorption (mg)=(Amount of Protein Before Adsorption in 1 mg/ml×40 ml)−(Amount of Protein Not Adsorbed).

Protein Adsorptivity (mg protein/g dry weight)=(Adsorption in mg)/(Weight of Sample (g)×(1×Water Content)

The results of experimentation are reported in below.

| | |
|---|---|
| Weight of the sample used | 0.7233 g |
| Absorbance of blank | 0.4838 (Abs280 nm) |
| Absorbance of the test liquid | 0.1693 |
| Total weight of the test liquid | 85.5 ml |
| Sample for measuring water content | |
| Weight before drying | 0.3124 g |
| Weight after drying | 0.2808 g |
| Water content | 0.101 |
| Adsorption | 10.7 mg |
| Albumin absorptivity | 16.4 mg albumin/g sample (d.W.) |

EXAMPLE 2 Polypetide Adsorption Test

Polypeptone (made by Nippon Seiyaku K.K.) is dissolved in deionized water and regulated to a concentration of 0.25% (w/v) at about pH 6.9.

Eighty (80) ml of the 0.25 polypeptone solution are poured in each of two 100-ml volume flasks, one of which is used as a blank. Put in another flask is the OH type of sample.

After gentle stirring, the flasks are allowed to stand overnight. The carriers are treated through a glass filter and washed with several portions of deionized water. After that, the filtrate combined with the washings is regulated with 0.1 N HCl to pH 7.0 to measure their total weight. By colorimetry, the absorbances of the blank and test liquid are measured at 280 nm to calculate their adsorptivities according to the procedure of Example 1.

The results are reported below.

| | |
|---|---|
| Weight of the sample used | 0.2004 g |
| Absorbance of blank | 1.3342 (Abs280 nm) |
| Absorbance of the test liquid | 0.7493 |
| Total weight of the test liquid | 132 ml |
| Sample for measuring water content | |
| Weight before drying | 0.2550 g |
| Weight after drying | 0.2327 g |
| Water content | 0.087 |
| Adsorption | 14.7 mg |
| Polypeptone Adsorptivity | 80.3 mg polypeptone/g sample (d.W.) |

EXAMPLE 3 Amino Acid Adsorption Test

An amino acid brandnamed as L-Tylosine (made by Wako Junyaku K.K.) is dissolved in a small amount of 0.1N sodium hydroxide and then dissolved in deionized water to a concentration of 0.0625% (w/v). The pH of the solution, which varies more or less depending upon the amount of sodium hydroxide, lies in the range of 11.5 to 12.

Eighty (80) ml of the 0.0625% Tylosine solution are poured in each of two 100-ml volume flasks, one of which is used as a blank. Put in another flask is the OH type of sample.

After gentle stirring, the flasks are allowed to stand overnight. The carriers are treated through a glass filter and washed with several portions of deionized water. After that, the filtrate combined with the washings is regulated to pH 11.5 to 12 to measure their total weight. By colorimetry, the absorbances of the blank and test liquid are measured at 293 nm to calculate their adsorptivities according to the procedure of Example 1.

The results are reported below.

| | |
|---|---|
| Weight of the sample used | 0.3988 g |
| Absorbance of blank | 0.7751 (Abs293 nm) |
| Absorbance of the test liquid | 0.4526 |
| Total weight of the test liquid | 130 ml |
| Sample for measuring water content | |
| Weight before drying | 0.2550 g |
| Weight after drying | 0.2327 g |
| Water content | 0.087 |
| Adsorption | 2.6 mg |
| Amino Acid Adsorptivity | 7.0 mg Tylosine/g sample (d.W.) |

EXAMPLE 4 Pigment Adsorption Test

Test were performed with commercially available food pigments (esculent blue and red) having the following components.

| | |
|---|---|
| Esculent Blue (made by Ogura Shokuhin Kako K.K.) | |
| Esculent Blue No. 1 | 5% |
| Esculent Yellow No. 4 | 3% |
| Dextrin | 92% |
| Esculent Red (made by Ogura Shokuhin Kako K.K.) | |
| Esculent Red No. 3 | 7% |
| Dextrin | 93% |

The esculent blue and red pigments are both dissolved in deionized water to a concentration of 0.25% (w/v).

Two hundred (200) ml of the 0.25% pigment solution are poured in each of two 300 ml volume flasks, one of which is used as a blank. Put in another flask is the OH type of sample.

After gentle stirring, the flasks are allowed to stand for 2 or 3 days. The carriers are treated through a glass filter and washed with several portions of deionized water to remove portions of the pigments not adsorbed. The filtrate is combined with the washings to prepare a test liquid, the total weight of which is then measured.

By colorimetry, the absorbances of the blank and test liquid are measured to calculate their adsorptivities according to the procedures of Example 1.

Absorbance determination is carried out at 630 nm with Esculent Blue No. 1 and at 410 nm with Esculent Yellow No. 4 for the food blue pigment; and at 526 nm with Esculent Red No. 3 for the food red pigment.

The results are set out below.

| | |
|---|---|
| Esculent Blue | |
| Weight of the sample used | 0.0415 g |
| Total weight of the test liquid | 180 ml |
| Blue No. 1 | |
| Blank Absorbance | 15.07 (Abs.630 nm) |
| Absorbance of the test liquid | 13.34 |
| Yellow No. 4 | |
| Blank Absorbance | 4.03 (Abs.410 nm) |
| Absorbance of the test liquid | 2.577 |
| Esculent Red | |
| Weight of the sample used | 0.0415 g |
| Total weight of the test liquid | 180 ml |
| Red No. 3 | |
| Blank Absorbance | 14.87 (Abs.526 nm) |
| Absorbance of the test liquid | 6.24 |
| Sample for measuring water content | |
| Weight before drying | 0.2099 g |
| Weight after drying | 0.1928 g |
| Water content | 0.081 |

-continued

| | |
|---|---|
| Adsorption of Blue No. 1 | 3.4 mg |
| Adsorption of Yellow No. 4 | 6.5 mg |
| Adsorption of Esculent Blue (Adsorptions of Blue No. 1 + Yellow No. 4) | 9.9 mg |
| Adsorptivity of Esculent Red | 25.5 mg |
| Adsorptivity of Esculent Blue Pigment | 259.6 mg pigment/g sample (d.W.) |
| Adsorptivity of Esculent Red Pigment | 673.1 mg pigment/g sample (d.W.) |

Examples 5-9 are given for the purpose of showing some embodiments of the animal cell culture carrier according to this invention. However, it is understood that the present invention is not limited thereto whatsoever.

EXAMPLE 5

Polyethyleneimine was covalently bonded to a marcerized, open-pore foamed cellulose material by way of epichlorohydrin to prepare an animal cell culture carrier material. The polyethyleneimine used had a molecular weight of 10,000, and the foamed cellulose material used was cut into a cubic piece having a i mm side, the size suitable for cell culture, (made by Sakai Engineering Co., Ltd.).

EXAMPLE 6

To obtain an animal cell culture carrier material or an ECTEOLA/cellulose combination, triethanolamine was covalently bonded to a mercerized, open-cell foamed cellulose material via epichlorohydrin. The foamed cellulose material used was cut into the same size as referred to in Example 1.

EXAMPLE 7

A mercerized, open-pore foamed cellulose material was allowed to react with monochloroacetic acid to prepare an animal cell culture carrier material with the carboxymethyl groups introduced in it. The foamed cellulose material was cut into the same size a referred to in Example 1.

EXAMPLE 8

A mercerized, open-pore foamed cellulose material was allowed to react with monochloroacetic acid into carboxymethylcellulose, in which polyethyleneimine was then introduced by electrostatic attraction, thereby preparing an animal cell culture carrier material. The polyethyleneimine used had a molecular weight of 70,000, and the open-pore cellulose material used was cut into the same size as referred to in Example 1.

EXAMPLE 9

An open-pore foamed cellulose material was out into a cubic piece having a 3-mm side, and was then formed into an animal cell culture carrier material by following the procedure of Example 1.

COMPARATIVE EXAMPLE 1

As an animal cell culture carrier material, use was made of Cytodex 2 made by Pharmacia Co., Ltd. in which N,N,N-trimethyl-2-hydroxy-aminopropyl groups were introduced onto the surfaces of crosslinked dextran beads.

COMPARATIVE EXAMPLE 2

As an animal cell culture carrier material, use was made of Dormacel 1 made by Pfeifer Langen Co., Ltd. in which dimers of diethylamino groups were introduced onto the surfaces of crosslinked dextran beads.

ILLUSTRATIVE EMBODIMENTS

Cell culture was performed with the carrier materials of Examples 5-9 and Comparative Examples 1-2. The number of immobilized cells and the concentration of valuable matters produced by them were determined after their proliferation had reached a steady state.

The number of cells were found by an erythrocytometer after the treatment of the carriers with trypsin. The media used were E-RDFs made by Kyokuto Seiyaku K.K., which received additionally cell proliferation promotors such as insulin, ethanolamine, transferrin and selenium. Immobilization zeroed on fibroblast and floating cells. The fibroblasts used were mouse L929 cell lines in which human erythropoetin genes (hereinafter EPO for short), and the floating cells used were antibody-producing mouse hybridoma 16-3F cell lines.

Experimentation relied upon stationary culture on petri plates and continuous culture in a transverse, internal cylinder revolution type of bioreactor (made by Sakai Engineering Co., Ltd.). For the bioreactor culture, the carrier were packed at 15% per volume of the culture solution.

EXPERIMENTAL RESULTS

As can be understood from Tables 1 and 2, the carriers according to this invention achieves much higher density cell immobilization and much higher productivity than do the conventional carrier.

TABLE 1

Densities of fibroblasts and concentration of EPO produced thereby.
(Cell density cells/ml)
(Concentration of EPO U/ml)

| | Cell density on petri plates | Bioreactor | |
|---|---|---|---|
| | | Cell density | Concentration of EPO |
| Example 5 | $8.3 \times 10^6$ | $1.6 \times 10^7$ | 6.5 |
| Example 6 | $2.2 \times 10^6$ | $5.6 \times 10^6$ | 2.1 |
| Example 7 | $1.5 \times 10^6$ | $5.0 \times 10^6$ | 2.0 |
| Example 8 | $3.3 \times 10^6$ | $9.4 \times 10^6$ | 3.8 |
| Example 9 | $7.5 \times 10^6$ | $1.8 \times 10^7$ | 6.6 |
| Comparative Example 1 | $8.8 \times 10^5$ | $1.8 \times 10^6$ | 1.1 |
| Comparative Example 2 | $1.7 \times 10^6$ | $1.6 \times 10^6$ | 0.9 |

TABLE 2

Density of floating cells and concentration of antibody produced thereby.
(Cell density cells/ml)
(Concentration of antibody mg/ml)

| | Cell density on petri plates | Bioreactor | |
|---|---|---|---|
| | | Cell density | Concentration of antibody |
| Example 5 | $1.3 \times 10^7$ | $8.5 \times 10^7$ | 10 |
| Example 6 | $4.1 \times 10^6$ | $4.0 \times 10^7$ | 5 |
| Example 7 | $2.3 \times 10^6$ | $5.0 \times 10^6$ | 3 |
| Example 8 | $3.9 \times 10^6$ | $9.4 \times 10^6$ | 6 |
| Example 9 | $8.4 \times 10^6$ | $7.0 \times 10^7$ | 10 |
| Comparative Example 1 | $4.4 \times 10^5$ | $2.8 \times 10^5$ | 0 |
| Comparative Example 2 | $2.8 \times 10^5$ | $6.2 \times 10^4$ | 0 |

TABLE 2-continued

Density of floating cells and concentration of
antibody produced thereby.
(Cell density cells/ml)
(Concentration of antibody mg/ml)

| | Bioreactor | |
|---|---|---|
| Cell density on petri plates | Cell density | Concentration of antibody |

Example 2

EFFECT OF THE INVENTION

As recounted above, we have successfully achieved an ion exchanger easy to handle, showing a much higher ion exchange capacity per unit weight and having a much larger surface area and a much higher physical strength by using an open-pore foamed cellulose material with ion-exchangeable functional groups introduced in it.

We have also achieved an animal cell culture carrier material enabling cell immobilization to be carried out at much higher densities. This is because it retains functional groups having an ion exchange capability best-suited for animal cells. Due to its specific construction, the present carrier material enables cells to be protected against physical impacts and media around cells to be rapidly metabolized, thus making it possible to effect mass-culture under severe conditions for it. Thus, the present carrier material can be used with diverse cell culture processes depending upon what they are industrially utilized for.

What we claim is:

1. An ultra-lightweight, open-pore foamed cellulose material with an increased surface area, comprising a three-dimensional network structure which, when swollen, has a particle diameter of 0.5 to 12.0 mm, a mean pore diameter of 0.1 to 1.7 mm, a specific surface area of 1.0 to 10.0 $m^2/g$, a true density of 1.4 to 1.6 $g/cm^3$ and a porosity of 90% or greater, wherein ion-exchangeable functional groups are introduced therein.

2. A cellulose material as claimed in claim 1, wherein the ion exchangeable functional groups are cationic polyethyleneimine.

* * * * *